US012594178B2

(12) United States Patent
Zhang et al.

(10) Patent No.: US 12,594,178 B2
(45) Date of Patent: Apr. 7, 2026

(54) REHABILITATION PROTECTIVE GEAR FOR PLANTAR FASCIITIS

(71) Applicant: Guangzhou New Design Biotechnology Co. Ltd., Guangzhou (CN)

(72) Inventors: Shaowei Zhang, Guangzhou (CN); Sile Zou, Guangzhou (CN)

(73) Assignee: Guangzhou New Design Biotechnology Co. Ltd., Guangzhou (CN)

( * ) Notice: Subject to any disclaimer, the term of this patent is extended or adjusted under 35 U.S.C. 154(b) by 71 days.

(21) Appl. No.: 18/582,924

(22) Filed: Feb. 21, 2024

(65) Prior Publication Data

US 2025/0262080 A1 Aug. 21, 2025

(51) Int. Cl.
*A61F 5/01* (2006.01)

(52) U.S. Cl.
CPC .................................. *A61F 5/0111* (2013.01)

(58) Field of Classification Search
CPC ..... A61F 5/0111; A61F 5/0113; A61F 5/0116; A61F 5/3769; A61F 5/3776; A61F 5/3792; A63B 23/08; A63B 23/085; A63B 21/04; A63B 21/0407; A63B 21/0442; A63B 21/0557; A43C 7/00; A43C 7/04; A43C 7/08; A43C 7/10
See application file for complete search history.

(56) References Cited

U.S. PATENT DOCUMENTS

| | | | | |
|---|---|---|---|---|
| 5,421,822 A * | 6/1995 | Wang | .................... | A61F 5/0111 602/27 |
| 6,056,712 A * | 5/2000 | Grim | .................... | A61F 5/0127 602/23 |
| 7,354,413 B2 * | 4/2008 | Fisher | ................... | A61F 5/0113 602/29 |
| 8,114,042 B2 * | 2/2012 | Klotz | .................... | A61F 5/0113 2/467 |
| 2012/0029404 A1 * | 2/2012 | Weaver | ................. | A61F 5/0111 602/27 |
| 2012/0065564 A1 * | 3/2012 | Hoffmeier | ............. | A61F 5/0113 602/28 |

(Continued)

FOREIGN PATENT DOCUMENTS

| | | |
|---|---|---|
| CN | 211723580 U | 10/2020 |
| CN | 114468471 A | 5/2022 |

*Primary Examiner* — Alireza Nia
*Assistant Examiner* — Gina Mccarthy
(74) *Attorney, Agent, or Firm* — Westbridge IP LLC

(57) ABSTRACT

A rehabilitation protective gear for plantar fasciitis includes a wearable main body, including a foot board for supporting a sole, and a peroneal guard plate integrally formed on the foot board for extending along a calf; a toe sleeve, detachably disposed at a front end of the foot board; and a traction structure, including a traction rope and a locking structure, one end of the traction rope being threaded in the toe sleeve, and the other end thereof being mounted on the peroneal guard plate. By pulling the traction rope, the toe sleeve is driven to tilt upwards, thereby driving toe ends of a foot body to be upturned. The locking structure is configured to cooperate with the traction rope to lock or unlock the traction rope subjected to length adjustment. The rehabilitation protective gear can improve stretching and comfort, promoting recovery of patients with plantar fasciitis.

6 Claims, 4 Drawing Sheets

(56) References Cited

U.S. PATENT DOCUMENTS

| 2014/0276320 | A1* | 9/2014 | Faux | A61F 5/0113 |
| | | | | 602/28 |
| 2018/0042752 | A1* | 2/2018 | Omarsson | A61F 5/0113 |
| 2019/0269558 | A1* | 9/2019 | Sheehan | A61F 5/0118 |
| 2020/0375776 | A1* | 12/2020 | Thor | A61F 5/0111 |
| 2021/0169673 | A1* | 6/2021 | Keegan | A61F 5/0127 |
| 2022/0110776 | A1* | 4/2022 | Darby | A61F 5/0111 |

* cited by examiner

REHABILITATION PROTECTIVE GEAR FOR PLANTAR FASCIITIS

TECHNICAL FIELD

The present application relates to the technical field of massage equipment, and in particular, to a rehabilitation protective gear for plantar fasciitis.

BACKGROUND

Plantar fasciitis is caused by aseptic inflammation of the plantar tendon or fascia. The most common symptoms are pain and discomfort in the heel, with a tenderness point often located at a part of the sole near the heel. Sometimes the tenderness is severe and persistent, and some patients may experience pain in both the arch and forefoot.

The existing rehabilitation protective gear for plantar fasciitis has a structure designed for plantar fasciitis, but the overall wrapping feeling of the structure is not strong, and the stretching feeling thereof is generally insufficient. In a stretching process, the toes are uncomfortable due to being compressed or pinched, which is not conducive to the rehabilitation of patients with plantar fasciitis.

SUMMARY

In view of the above, the present application provides a rehabilitation protective gear for plantar fasciitis to enhance the overall wrapping feeling, and improve the stretching feeling and the comfort of use, thus promoting the recovery of patients with plantar fasciitis.

The technical solution adopted in the present application is as follows.

The present application provides a rehabilitation protective gear for plantar fasciitis, which includes:

a wearable main body, including a foot board for supporting a sole, and a peroneal guard plate integrally formed on the foot board for extending along a calf;

a toe sleeve, detachably disposed at a front end of the foot board; and a traction structure, including a traction rope and a locking structure, one end of the traction rope is threaded on the toe sleeve, and the other end thereof is mounted on the peroneal guard plate; by pulling the traction rope, the toe sleeve is driven to tilt upwards, thereby driving toe ends of a foot body to be upturned; and the locking structure is configured to cooperate with the traction rope to lock or unlock the traction rope subjected to length adjustment.

Further, the rehabilitation protective gear for plantar fasciitis includes a connecting pad, one end of the connecting pad is connected to the foot board, and the other end thereof is connected to the toe sleeve.

Further, the connecting pad can be mounted on the foot board in a position-adjustable manner along the foot length direction.

Further, the connecting pad includes a pad body connected to an interior of the toe sleeve, and a connecting band connected to the pad body, where a flexible band body or an elastic strip that can be swung upwards and bent may be employed as the connecting band.

Further, a plurality of position adjusting holes are reserved in the foot board along the foot length direction, a bottom surface of the connecting band has connecting columns, which are snapped into the position adjusting holes to achieve a connection between the foot board and the connecting pad, and the length of the connecting band connected to the foot board is adjusted by selectively snapping the connecting columns into the position adjusting holes.

Further, a plurality of protrusions are formed on a bottom surface of the pad body, and a plurality of concave holes are formed in the toe sleeve correspondingly; and the protrusions of the pad body are correspondingly sleeved inside the concave holes, so that the toe sleeve is connected to the connecting pad.

Further, the locking structure includes a rotary knob, which is mounted on the peroneal guard plate; and the traction rope is threaded on the toe sleeve and in the rotary knob, so that the traction rope is contracted by rotating the rotary knob and thus stretches the toe sleeve upwards.

Further, the locking structure includes a velcro tape, a buckle hole is formed in the peroneal guard plate, the velcro tape is formed at one end of the traction rope, and the end of the traction rope with the velcro tape passes through the buckle hole and is then bonded after threading out at a length of adjustment required, thereby fixing a traction end of the traction rope.

Further, the rehabilitation protective gear for plantar fasciitis includes a heel pad, which is mounted on the foot board and is configured to support the sole of a person who wears the protective gear.

Further, the wearable main body includes a housing layer, and an inner lining layer attached to an inner side of the housing layer.

Further, the rehabilitation protective gear for plantar fasciitis includes a first strap, one end of which is connected to the foot board and located on the side opposite to the peroneal guard plate, and the first strap is configured to bind the peroneal guard plate to the calf by bypassing the instep.

Further, the rehabilitation protective gear for plantar fasciitis includes a second strap, one end of which is connected to a top end of the peroneal guard plate, the second strap cooperates with the peroneal guard plate to wrap the calf.

Further, the toe sleeve is a hard sleeve, and includes a bottom plate and an arched portion connected to the bottom plate; and a space for accommodating toes is formed between the bottom plate and the arched portion.

Compared with the prior art, the rehabilitation protective gear for plantar fasciitis according to the present application is equipped with a heel pad, the first strap, the second strap, the connecting pad, the toe sleeve, the rotary knob and the traction rope in a cooperative manner on the wearable main body. When in use, the wearable main body is sleeved outside a foot, toes are located on the connecting pad, the first strap is bypassed from the instep and tied tightly after being wound around the calf for a circle, and the calf is bound to the peroneal guard plate by the second strap; and the rotary knob is rotated to drive the traction rope to contract, so that the toe sleeve drives the toes to stretch upwards. The toes are stretched under the support of the toe sleeve, and thus there is no squeezing or discomfort between the toes, which improves the stretching feeling and the comfort of use. The toe sleeve is stretched by the rotary knob driving the traction rope to contract, which facilitates adjustment and can achieve fine adjustment. The heel pad is configured to support, so that the overall wrapping feeling is improved. The rehabilitation protective gear for plantar fasciitis according to the present application is convenient to wear and has a significant stretching effect, which is beneficial to promoting the recovery of the patients with plantar fasciitis.

BRIEF DESCRIPTION OF THE DRAWINGS

The accompanying drawings are intended to provide a further understanding of the present application and constitute a part of the Description. They are used together with the specific embodiments below to explain the present application, but should not be construed as a limitation on the present application.

DETAILED DESCRIPTION OF THE EMBODIMENTS

Specific embodiments of the present application are described in detail below with reference to the accompanying drawings. It should be understood that the specific embodiments described herein are only used to illustrate and explain the present application, and are not intended to limit the present application.

Figure 1:
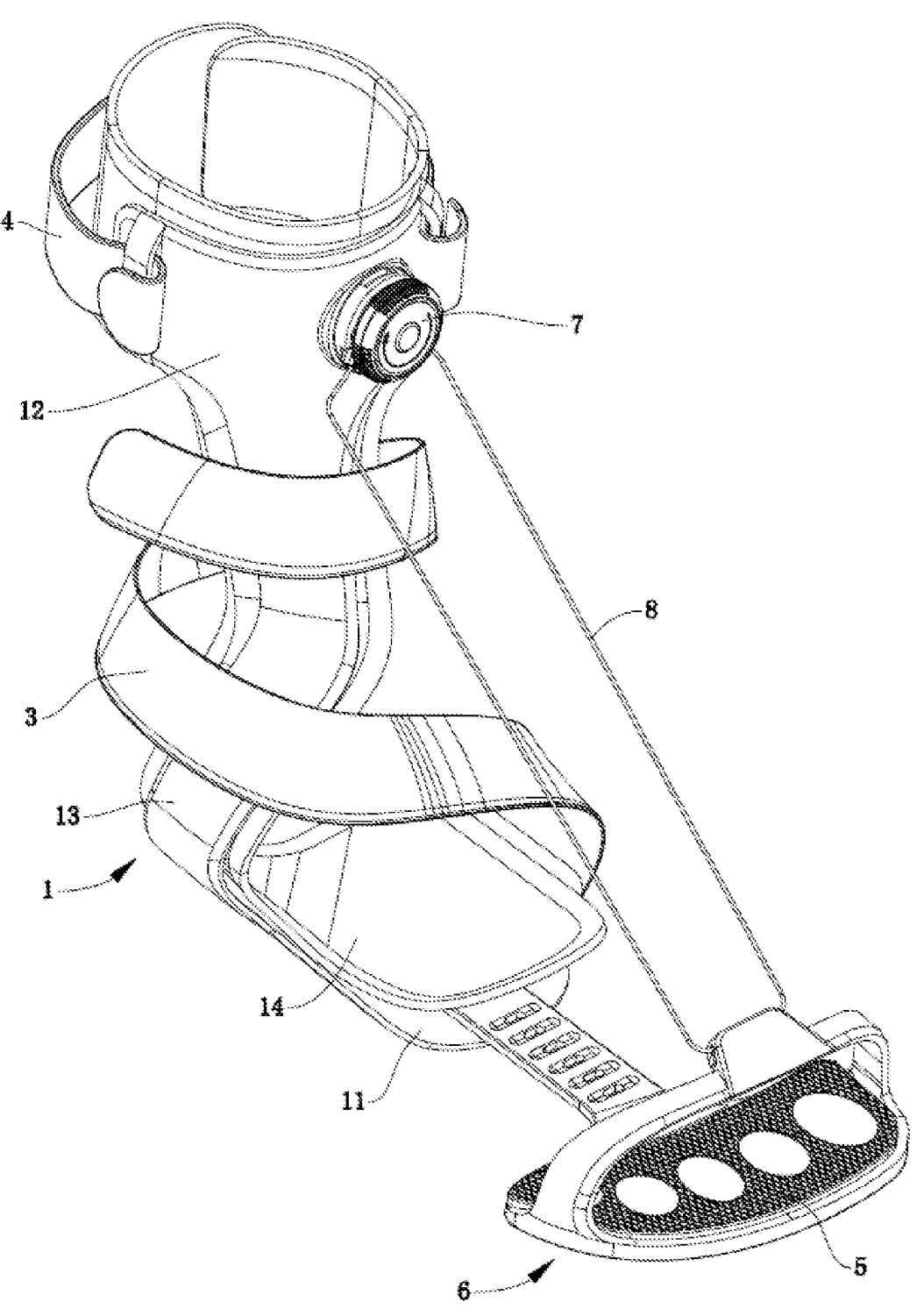
FIG. 1 is a stereoscopic view of a rehabilitation protective gear for plantar fasciitis according to the present application from the view of a first perspective.
Figure 2:
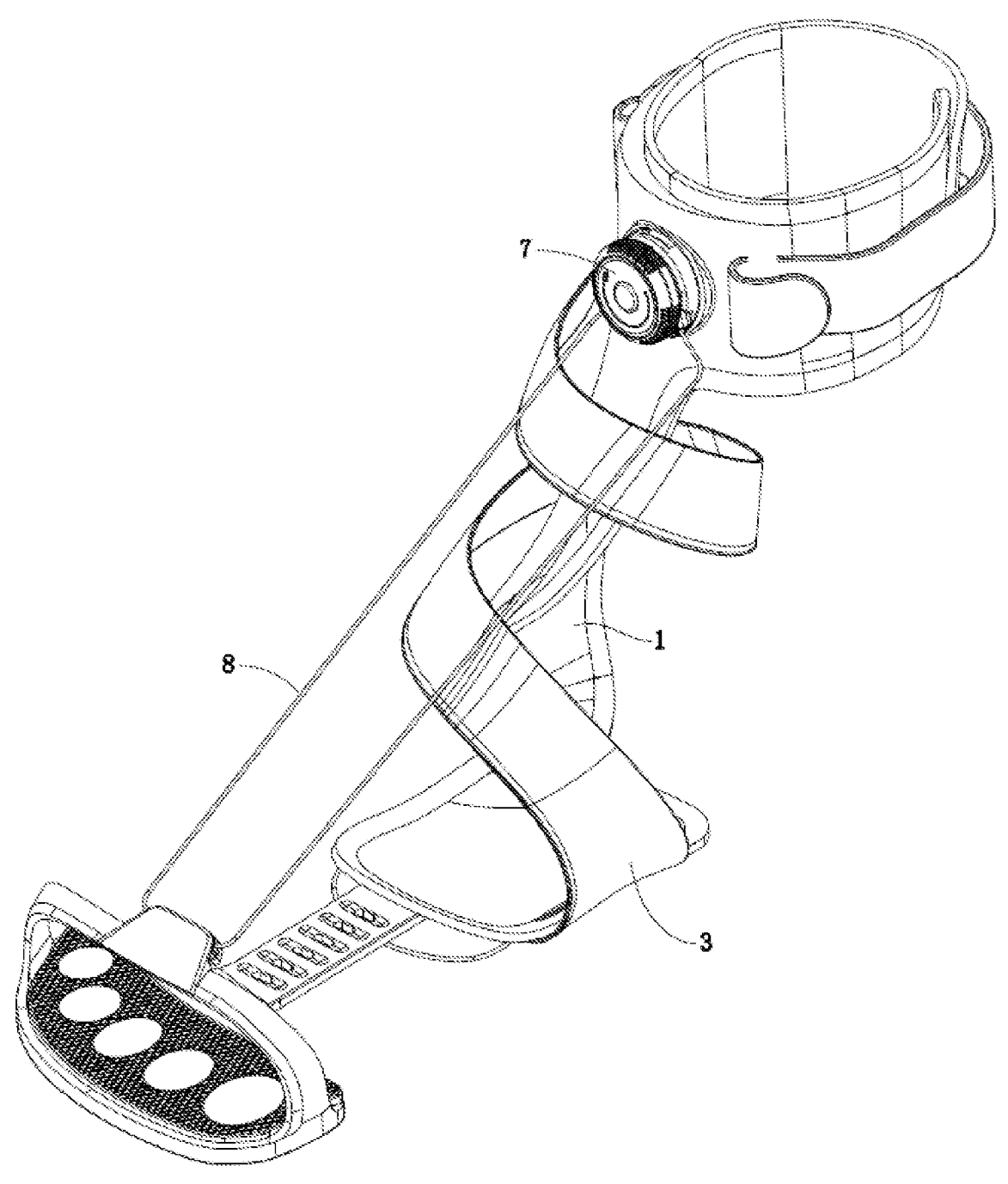
FIG. 2 is a stereoscopic view of the rehabilitation protective gear for plantar fasciitis according to the present application from the view of a second perspective.
Figure 3:
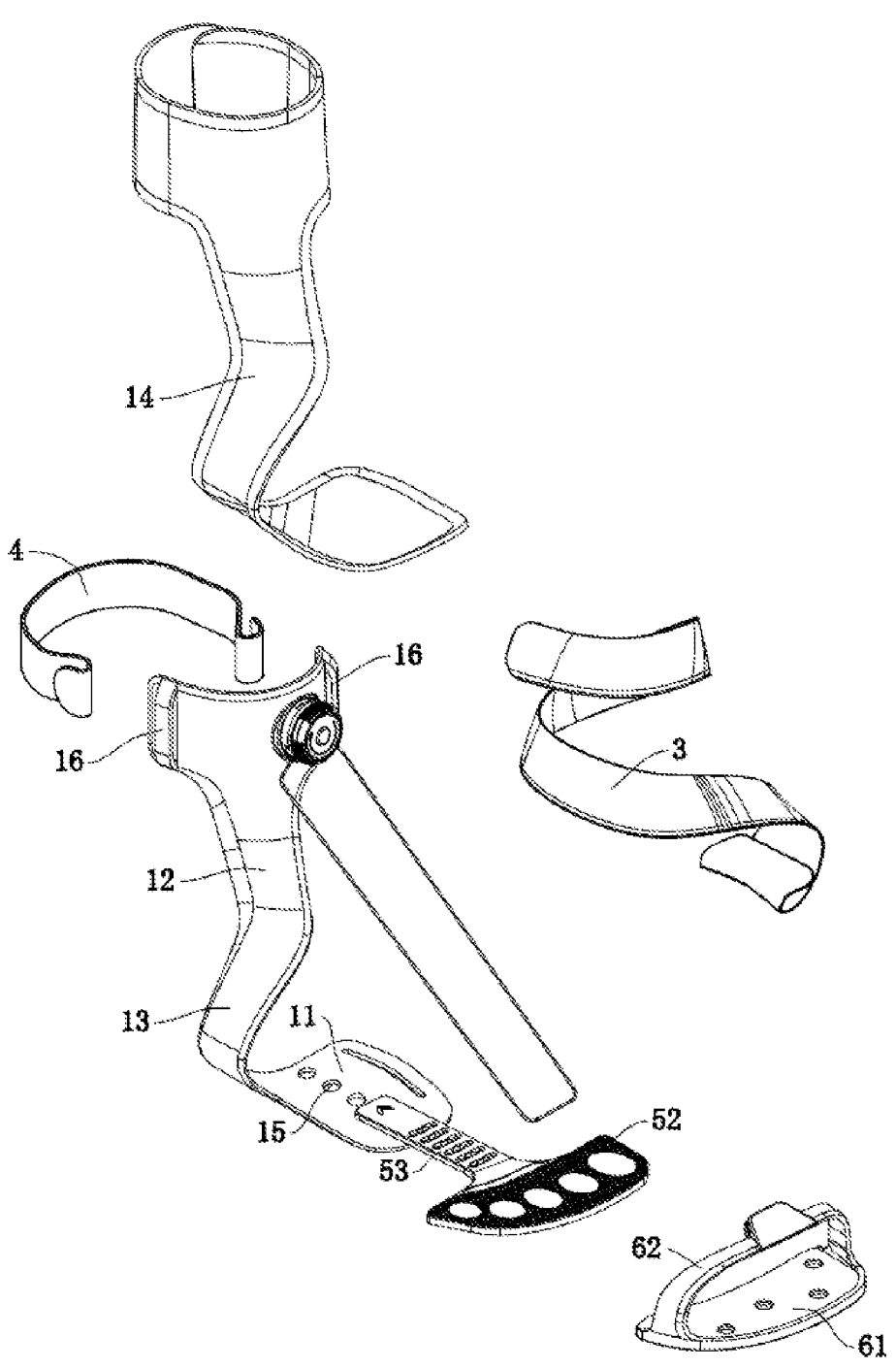
FIG. 3 is an exploded view of the rehabilitation protective gear for plantar fasciitis according to the present application from the view of a first perspective.
Figure 4:
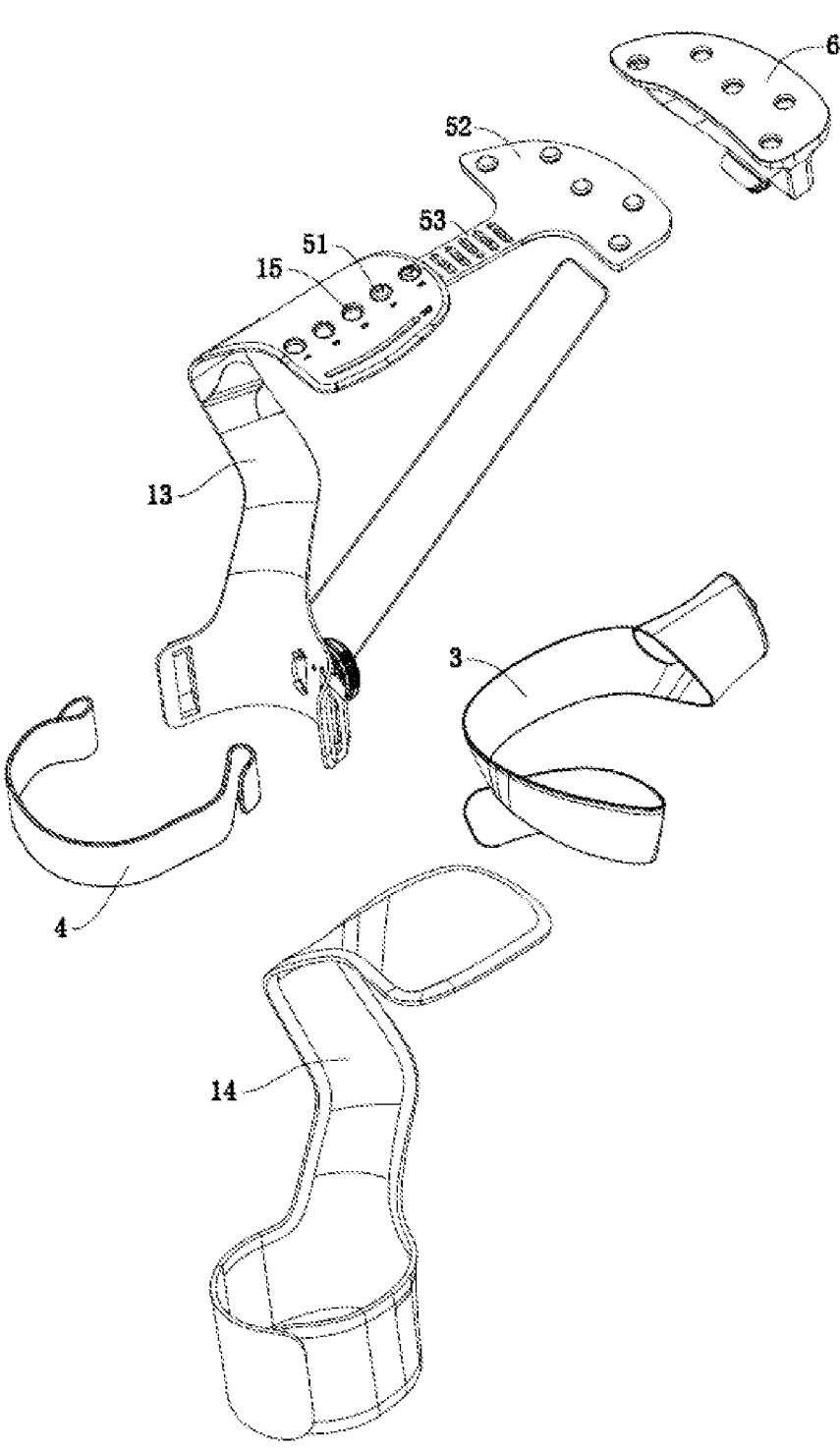
FIG. 4 is an exploded view of the rehabilitation protective gear for plantar fasciitis according to the present application from the view of a second perspective.

As shown in FIG. 1 to FIG. 4, the present application provides a rehabilitation protective gear for plantar fasciitis, which includes a wearable main body 1, a first strap 3, a second strap 4, a connecting pad 5, a toe sleeve 6, and a traction structure. The wearable main body 1 includes a foot board 11 for supporting a sole, and a peroneal guard plate 12 integrally formed on the foot board 11 for extending along a calf; and specifically, the peroneal guard plate 12 is integrally formed on a side of a rear end (corresponding to a heel) of the foot board 11. One end of the first strap 3 is connected to the foot board 11 and located on the side opposite to the peroneal guard plate 12, and the first strap 3 is configured to bind the peroneal guard plate 12 to the calf by bypassing the instep. One end of the second strap 4 is connected to a top end of the peroneal guard plate 12, and the second strap 4 cooperates with the peroneal guard plate 12 to wrap the calf. One end of the connecting pad 5 is connected to the foot board 11, and the other end thereof is connected to the toe sleeve 6. The traction structure includes a traction rope 8 and a locking structure, where one end of the traction rope 8 is threaded on the toe sleeve 6, and the other end thereof is mounted on the peroneal guard plate 12; by pulling the traction rope 8, the toe sleeve 6 is driven to tilt upwards, thereby driving toe ends of a foot body to be upturned; and the locking structure is configured to cooperate with the traction rope 8 to lock or unlock the traction rope 8 subjected to length adjustment.

When in use, the wearable main body 1 is sleeved outside a foot, toes are located inside the toe sleeve 6, the first strap 3 is bypassed from the instep and tied tightly after being wound around the calf for a circle, and the calf is bound to the peroneal guard plate 12 by the second strap 4; and the traction rope 8 of the traction structure is contracted, so that the toe sleeve 6 drives the toes to stretch upwards. The toes are stretched under the support of the toe sleeve 6, and thus there is no squeezing or discomfort between the toes, which improves the stretching feeling and the comfort of use. The rehabilitation protective gear for plantar fasciitis according to the present application is convenient to wear and has a significant stretching effect, which is beneficial to promoting the recovery of the patients with plantar fasciitis.

In this embodiment, the wearable main body 1 includes a housing layer 13, and an inner lining layer 14 attached to an inner side of the housing layer 13 so as to achieve wearing comfort. The housing layer 13 may be made of plastic to integrally form the foot board 11 and the peroneal guard plate 12.

The toe sleeve 6 is detachably disposed at a front end of the foot board 11, or may be connected to the foot board 11 by means of the connecting pad 5, one end of the connecting pad 5 is connected to the foot board 11, and the other end thereof is connected to the toe sleeve 6. Preferably, the toe sleeve 6 is connected to the foot board 11 by means of the connecting pad 5.

In order to adapt to the wearing of people with different foot lengths, the toe sleeve 6 is mounted on the foot board 11 in a position-adjustable manner along the foot length direction by means of the connecting pad 5. As an adjustable mounting way, optionally, a plurality of position adjusting holes 15 are reserved in the foot board 11 along the foot length direction, connecting columns 51 are formed on a bottom surface of one end of the connecting pad 5, and the connecting columns 51 are snapped into the position adjusting holes 15. The position adjusting holes 15 at different positions are selected for snapping the connecting columns 51, so that the adjustment of different lengths can be implemented.

The connecting pad 5 includes a pad body 52 connected to the toe sleeve 6, and a connecting band 53 connected to the pad body 52. The plurality of connecting columns 51 are disposed on the connecting band 53. The connecting band 53 is narrower than the pad body 52, making it easier for the toe sleeve 6 to bend when stretched upwards. A flexible band body or an elastic strip that can be swung upwards and bent may be employed as the connecting band 53. The pad body 52 may be made of elastic materials such as silicone.

Preferably, the toe sleeve 6 is a hard sleeve for easy traction. The toe sleeve 6 includes a bottom plate 61 and an arched portion 62 connected to the bottom plate 61, where a space for accommodating toes is formed between the bottom plate 61 and the arched portion 62. The pad body 52 is connected to the bottom plate 61, and the connection mode is optional, a plurality of protrusions are formed on a bottom surface of the pad body 52, a plurality of concave holes are formed in the toe sleeve 6 correspondingly, and the protrusions of the pad body 52 are correspondingly sleeved inside the concave holes, so that the toe sleeve 6 is connected to the connecting pad 5. The traction rope 8 is provided at a middle position of the arched portion 62. The toe sleeve 6 is matched with the arched portion 62 by arranging the bottom plate 61, the bottom plate 61 can support the toes, and the arched portion 62 is convenient for connecting the traction rope 8 to stretch.

The product with the locking structure preferably employing a rotary knob 7 and the traction rope 8 which cooperate with each other is the prior art, and thus can be directly purchased; and for example, a rope adjustment device disclosed in the announcement number CN210382859U, or a knob-type rope adjuster disclosed in the publication number CN115028027A may be used as the locking structure. The rotary knob 7 is mounted on the peroneal guard plate 12, and the traction rope 8 is threaded on the toe sleeve 6 and in the rotary knob 7, so that the traction rope 8 is contracted by rotating the rotary knob 7 and thus stretches the toe sleeve 6 upwards. Release of the traction rope 8 is achieved by pressing or reversely rotating the rotary knob 7.

It can be understood that the locking structure may also be fixed by using a velcro tape bonding method. A buckle hole is formed in the peroneal guard plate 12, the velcro tape is formed at one end of the traction rope 8, and the end of the traction rope 8 with the velcro tape passes through the buckle hole and is then bonded after threading out at a length of adjustment required, thereby fixing a traction end of the traction rope 8.

It can be understood that after being bonded, the first strap 3 and the second strap 4 may also be fixed using the velcro tape bonding method. Connecting buckles 16 are respectively disposed at both sides of the top end of the peroneal guard plate 12, and two ends of the second strap 4 are bonded to the connecting buckles 16 by means of velcro tapes, which facilitates the disassembly and assembly of the second strap 4. One end of the first strap 3 is bonded to a connecting hole of the foot board 11 by means of a velcro tape, and the other end of the first strap 3 is bonded to the first strap 3 by means of a velcro tape.

It can be understood that the rehabilitation protective gear for plantar fasciitis may be provided with a heel pad, which is mounted on the foot board 11, specifically mounted on the inner lining layer 14 of the foot board 11, and is configured to support the sole of a person who wears the protective gear. The heel pad provides support, enhancing the overall sense of wrapping and comfort.

To sum up, when the rehabilitation protective gear for plantar fasciitis according to the present application is in use, the wearable main body 1 is sleeved outside a foot, toes are located on the connecting pad 5, the first strap 3 is bypassed from the instep and tied tightly after being wound around the calf for a circle, and the calf is bound to the peroneal guard plate 12 by the second strap 4; and the traction rope 8 is contracted to allow the toe sleeve 6 to drive the toes to stretch upwards. The toes are stretched under the support of the toe sleeve 6, and thus there is no squeezing or discomfort between the toes, which improves the stretching feeling and the comfort of use. Particularly, the toe sleeve 6 is stretched by the rotary knob 7 driving the traction rope 8 to contract, which greatly facilitates adjustment and can achieve fine adjustment. The rehabilitation protective gear for plantar fasciitis according to the present application is convenient to wear and has a significant stretching effect, which is beneficial to promoting the recovery of the patients with plantar fasciitis.

Any combination of various different embodiments according to the present application, as long as it does not violate the idea created by the present application, shall be regarded as the content disclosed by the present application. Within the scope of the technical concept of the present application, any combination of multiple simple variations and different embodiments of the technical solution that do not violate the ideas created in the present application shall be within the scope of protection of the present application.

What is claimed is:

1. A rehabilitation protective gear for plantar fasciitis, comprising:

a wearable main body, comprising a foot board for supporting a sole, and a peroneal guard plate integrally formed on the foot board for extending along a calf;

a toe sleeve, detachably disposed at a front end of the foot board; and a traction structure, comprising a traction rope and a locking structure, wherein one end of the traction rope is threaded on the toe sleeve, and another end of the traction rope is mounted on the peroneal guard plate; by pulling the traction rope, the toe sleeve is driven to tilt upwards, thereby driving toe ends of a foot body to be upturned; and the locking structure is configured to cooperate with the traction rope to lock or unlock the traction rope subjected to length adjustment;

the rehabilitation protective gear for plantar fasciitis further comprises a connecting pad, which is capable of being mounted on the foot board in a position-adjustable manner along the foot length direction, one end of the connecting pad is connected to the foot board, and another end of the connecting pad is connected to the toe sleeve;

the connecting pad comprises a pad body connected to an interior of the toe sleeve, and a connecting band connected to the pad body, a flexible band body or an elastic strip that is capable of being swung upwards and bent is employed as the connecting band; and a plurality of position adjusting holes are reserved in the foot board along the foot length direction, a bottom surface of the connecting band has connecting columns, which are snapped into the position adjusting holes to achieve a connection between the foot board and the connecting pad, and a length of the connecting band connected to the foot board is adjusted by selectively snapping the connecting columns into the position adjusting holes.

2. The rehabilitation protective gear for plantar fasciitis according to claim 1, wherein a plurality of protrusions are formed on a bottom surface of the pad body, and a plurality of concave holes are formed in the toe sleeve correspondingly; and the plurality of protrusions of the pad body are correspondingly sleeved inside the concave holes, so that the toe sleeve is connected to the connecting pad.

3. The rehabilitation protective gear for plantar fasciitis according to claim 1, wherein the locking structure comprises a rotary knob, which is mounted on the peroneal guard plate; and the traction rope is threaded on the toe sleeve and in the rotary knob, so that the traction rope is contracted by rotating the rotary knob and thus stretches the toe sleeve upwards.

4. The rehabilitation protective gear for plantar fasciitis according to claim 1, wherein the wearable main body comprises a housing layer, and an inner lining layer attached to an inner side of the housing layer.

5. The rehabilitation protective gear for plantar fasciitis according to claim 1, comprising a first strap, one end of the first strap being connected to the foot board and located on the side opposite to the peroneal guard plate, the first strap being configured to bind the peroneal guard plate to the calf by bypassing the instep; and a second strap, one end of the second strap being connected to a top end of the peroneal guard plate, the second strap cooperating with the peroneal guard plate to wrap the calf.

6. The rehabilitation protective gear for plantar fasciitis according to claim 1, wherein the toe sleeve has a solid surface, and comprises a bottom plate and an arched portion connected to the bottom plate, wherein a space for accommodating toes is formed between the bottom plate and the arched portion.

* * * * *